(12) United States Patent
Micheli

(10) Patent No.: US 7,922,911 B2
(45) Date of Patent: *Apr. 12, 2011

(54) SYSTEMS AND METHODS FOR PERITONEAL DIALYSIS

(75) Inventor: Brian R. Micheli, Wadsworth, IL (US)

(73) Assignees: Baxter International Inc., Deerfield, IL (US); Baxter Healthcare S.A., Glattpark (Opfikon) (CH)

(*) Notice: Subject to any disclaimer, the term of this patent is extended or adjusted under 35 U.S.C. 154(b) by 0 days.

This patent is subject to a terminal disclaimer.

(21) Appl. No.: 12/474,481

(22) Filed: May 29, 2009

(65) Prior Publication Data

US 2009/0264812 A1 Oct. 22, 2009

Related U.S. Application Data

(63) Continuation of application No. 11/690,584, filed on Mar. 23, 2007, now abandoned, which is a continuation of application No. 10/623,317, filed on Jul. 17, 2003, now Pat. No. 7,208,092.

(60) Provisional application No. 60/397,045, filed on Jul. 19, 2002.

(51) Int. Cl.
*B01D 61/30* (2006.01)

(52) U.S. Cl. ........... 210/645; 210/195.2; 210/257.2; 210/258; 210/321.65; 210/650; 210/805; 604/29; 604/30

(58) Field of Classification Search .......... 210/87, 210/90, 97, 167, 175, 182, 184, 194, 195.1, 210/195.2, 257.2, 258, 259, 321.65, 321.71, 210/637, 641, 654–647, 651, 739, 741, 774, 210/805, 806; 604/4.01, 5.01, 5.04, 6.09, 6.11, 29, 30

See application file for complete search history.

(56) References Cited

U.S. PATENT DOCUMENTS

| | | | |
|---|---|---|---|
| 2,122,509 A | 7/1938 | Beliaff | |
| 2,529,028 A | 7/1947 | Landon | |
| 3,332,737 A | 7/1967 | Krause | |
| 3,388,803 A | 6/1968 | Scott | |
| 3,463,728 A | 8/1969 | Kolobow et al. | |
| 3,485,245 A | 12/1969 | Lahr et al. | |
| 3,490,479 A | 1/1970 | Mott et al. | |
| 3,545,438 A | 12/1970 | De Vries | |

(Continued)

FOREIGN PATENT DOCUMENTS

DE 19828923 A1 1/2000

(Continued)

OTHER PUBLICATIONS

Roberts et al publication, "Innovative Peritoneal Dialysis: Flow-Thru and Dialysate Regeneration" from Scholary Review, ASAIO Journal 1999, pp. 372-378.*

(Continued)

*Primary Examiner* — Joseph W Drodge
(74) *Attorney, Agent, or Firm* — K&L Gates LLP

(57) ABSTRACT

Systems and methods relating to dialysis therapy, particularly continuous flow dialysis therapy, are provided. The present invention includes a single closed fluid path along which a minimal amount of therapy fluid including dialysate is fed into, continuously circulated and cleaned such that a therapeutic effective amount of solutes, excess water and the like can be removed from the patient connected to the closed fluid loop during treatment.

32 Claims, 2 Drawing Sheets

U.S. PATENT DOCUMENTS

| | | | |
|---|---|---|---|
| 3,608,729 A | 9/1971 | Haselden |
| 3,617,545 A | 11/1971 | Dubois et al. |
| 3,619,423 A | 11/1971 | Galletti et al. |
| 3,667,612 A | 6/1972 | Leonard |
| 3,669,878 A | 6/1972 | Marantz et al. |
| 3,669,880 A | 6/1972 | Marantz et al. |
| 3,682,817 A | 8/1972 | Marx |
| 3,697,418 A | 10/1972 | Johnson |
| 3,703,959 A | 11/1972 | Raymond |
| 3,707,967 A | 1/1973 | Kitrilakis et al. |
| 3,727,612 A | 4/1973 | Sayers et al. |
| 3,730,183 A | 5/1973 | Goldsmith et al. |
| 3,799,873 A | 3/1974 | Brown |
| 3,809,241 A | 5/1974 | Alvine |
| 3,825,493 A | 7/1974 | Brown et al. |
| 3,827,975 A | 8/1974 | Bizot et al. |
| 3,850,835 A | 11/1974 | Marantz et al. |
| 3,878,564 A | 4/1975 | Yao et al. |
| 3,884,808 A | 5/1975 | Scott |
| 3,911,915 A | 10/1975 | Seifter et al. |
| 3,926,797 A | 12/1975 | Gigou et al. |
| 3,939,069 A | 2/1976 | Granger et al. |
| 3,979,284 A | 9/1976 | Granger et al. |
| 3,989,622 A | 11/1976 | Marantz et al. |
| 4,000,072 A | 12/1976 | Sato et al. |
| 4,031,010 A | 6/1977 | Nose |
| 4,036,747 A | 7/1977 | Hori et al. |
| 4,081,372 A | 3/1978 | Atkin et al. |
| 4,115,259 A | 9/1978 | Bigi |
| 4,118,314 A | 10/1978 | Yoshida |
| 4,173,537 A | 11/1979 | Newhart et al. |
| 4,180,460 A | 12/1979 | Calari |
| 4,190,047 A | 2/1980 | Jacobsen et al. |
| 4,191,646 A | 3/1980 | Larsson et al. |
| 4,192,748 A | 3/1980 | Hyden |
| 4,194,536 A | 3/1980 | Stine et al. |
| 4,212,738 A | 7/1980 | Henne |
| 4,213,859 A | 7/1980 | Smakman et al. |
| 4,240,408 A | 12/1980 | Schael |
| 4,247,393 A | 1/1981 | Wallace |
| 4,256,718 A | 3/1981 | McArthur et al. |
| 4,267,047 A | 5/1981 | Henne et al. |
| 4,269,708 A | 5/1981 | Bonomini et al. |
| 4,276,175 A | 6/1981 | Bower |
| 4,293,762 A | 10/1981 | Ogawa |
| 4,303,521 A | 12/1981 | Lehmann |
| 4,308,255 A | 12/1981 | Raj et al. |
| 4,313,831 A | 2/1982 | Lehmann et al. |
| 4,338,190 A | 7/1982 | Kraus et al. |
| 4,360,507 A | 11/1982 | McArthur et al. |
| 4,364,747 A | 12/1982 | Blackshear, Jr. |
| 4,381,003 A | 4/1983 | Buoncristiani |
| 4,460,555 A | 7/1984 | Thompson |
| 4,464,563 A | 8/1984 | Jewett |
| 4,473,449 A | 9/1984 | Michaels et al. |
| 4,498,900 A | 2/1985 | Buoncristiani |
| 4,532,414 A | 7/1985 | Shah et al. |
| 4,542,015 A | 9/1985 | Smakman et al. |
| 4,581,141 A | 4/1986 | Ash |
| 4,586,920 A | 5/1986 | Peabody |
| 4,618,343 A | 10/1986 | Polaschegg |
| RE32,303 E | 12/1986 | Lasker et al. |
| 4,650,857 A | 3/1987 | May |
| 4,661,246 A | 4/1987 | Ash |
| 4,678,460 A | 7/1987 | Rosner |
| 4,680,445 A | 7/1987 | Ogawa |
| 4,684,460 A | 8/1987 | Issautier |
| 4,703,913 A | 11/1987 | Hunkapiller |
| 4,718,890 A | 1/1988 | Peabody |
| 4,735,609 A | 4/1988 | Comeau et al. |
| 4,747,822 A | 5/1988 | Peabody |
| 4,765,907 A | 8/1988 | Scott |
| 4,769,151 A | 9/1988 | Shouldice |
| 4,804,474 A | 2/1989 | Blum |
| 4,844,074 A | 7/1989 | Kurucz |
| 4,846,950 A | 7/1989 | Yao et al. |
| 4,847,470 A | 7/1989 | Bakke |
| 4,906,816 A | 3/1990 | van Leerdam |
| 4,976,683 A | 12/1990 | Gauthier et al. |
| 5,004,459 A | 4/1991 | Peabody et al. |
| 5,073,167 A | 12/1991 | Carr et al. |
| 5,125,069 A | 6/1992 | O'Boyle |
| 5,141,492 A | 8/1992 | Dadson et al. |
| 5,141,493 A | 8/1992 | Jacobsen et al. |
| 5,180,896 A | 1/1993 | Gibby et al. |
| 5,245,693 A | 9/1993 | Ford et al. |
| 5,277,820 A | 1/1994 | Ash |
| 5,284,470 A | 2/1994 | Beltz |
| 5,336,173 A | 8/1994 | Folden |
| 5,338,293 A | 8/1994 | Jeppsson et al. |
| 5,350,357 A | 9/1994 | Kamen et al. |
| 5,370,674 A | 12/1994 | Farrell |
| 5,381,510 A | 1/1995 | Ford et al. |
| 5,408,576 A | 4/1995 | Bishop |
| 5,420,962 A | 5/1995 | Bakke |
| 5,438,510 A | 8/1995 | Bryant et al. |
| 5,474,683 A * | 12/1995 | Bryant et al. .................. 210/646 |
| 5,498,338 A | 3/1996 | Kruger et al. |
| 5,542,919 A | 8/1996 | Simon et al. |
| 5,544,684 A | 8/1996 | Robinette, III |
| 5,631,025 A * | 5/1997 | Shockley et al. .............. 424/678 |
| 5,641,405 A | 6/1997 | Keshaviah et al. |
| 5,643,201 A * | 7/1997 | Peabody et al. ................. 604/31 |
| 5,645,734 A | 7/1997 | Kenley et al. |
| 5,683,381 A | 11/1997 | Carr et al. |
| 5,685,988 A | 11/1997 | Malchesky |
| 5,690,614 A | 11/1997 | Carr et al. |
| 5,722,947 A | 3/1998 | Jeppsson et al. |
| 5,724,478 A | 3/1998 | Thweatt |
| 5,729,653 A | 3/1998 | Magliochetti et al. |
| 5,744,042 A | 4/1998 | Stange et al. |
| 5,762,782 A | 6/1998 | Kenley et al. |
| 5,776,091 A | 7/1998 | Brugger et al. |
| 5,790,752 A | 8/1998 | Anglin et al. |
| 5,816,779 A | 10/1998 | Lawless et al. |
| 5,836,908 A | 11/1998 | Beden et al. |
| 5,858,238 A | 1/1999 | McRea et al. |
| 5,873,853 A | 2/1999 | Keilman et al. |
| 5,875,282 A | 2/1999 | Jordan et al. |
| 5,902,336 A | 5/1999 | Mishkin |
| 5,919,369 A | 7/1999 | Ash |
| 5,921,951 A | 7/1999 | Morris |
| 5,938,634 A | 8/1999 | Packard |
| 5,944,684 A * | 8/1999 | Roberts et al. ............... 604/5.04 |
| 5,960,160 A | 9/1999 | Clark et al. |
| 5,980,481 A | 11/1999 | Gorsuch |
| 5,984,891 A | 11/1999 | Keilman et al. |
| 5,989,238 A | 11/1999 | Ginsburg |
| 5,989,423 A | 11/1999 | Kamen et al. |
| 6,069,343 A | 5/2000 | Kolowich |
| 6,074,359 A | 6/2000 | Keshaviah et al. |
| 6,129,699 A | 10/2000 | Haight et al. |
| 6,139,528 A | 10/2000 | Kistner et al. |
| 6,142,974 A | 11/2000 | Kistner et al. |
| 6,142,975 A | 11/2000 | Jalisi et al. |
| 6,146,359 A | 11/2000 | Carr et al. |
| 6,168,578 B1 | 1/2001 | Diamond |
| 6,175,688 B1 | 1/2001 | Cassidy et al. |
| 6,193,684 B1 | 2/2001 | Burbank et al. |
| 6,196,992 B1 | 3/2001 | Keilman et al. |
| 6,210,361 B1 | 4/2001 | Kamen et al. |
| 6,220,299 B1 | 4/2001 | Arvidsson et al. |
| 6,228,047 B1 | 5/2001 | Dadson |
| 6,229,957 B1 | 5/2001 | Baker |
| 6,234,991 B1 | 5/2001 | Gorsuch |
| 6,234,992 B1 | 5/2001 | Haight et al. |
| 6,236,809 B1 | 5/2001 | Cassidy et al. |
| 6,245,039 B1 | 6/2001 | Brugger et al. |
| 6,254,567 B1 | 7/2001 | Trea et al. |
| 6,261,261 B1 | 7/2001 | Gordon |
| 6,261,809 B1 | 7/2001 | Bertling et al. |
| 6,290,669 B1 | 9/2001 | Zicherman |
| 6,293,921 B1 | 9/2001 | Shinmoto et al. |
| 6,302,653 B1 | 10/2001 | Bryant et al. |
| 6,409,699 B1 | 6/2002 | Ash |
| 6,666,842 B1 * | 12/2003 | Sakai ............................. 604/29 |
| 6,976,973 B1 * | 12/2005 | Ruddell et al. .................. 604/29 |

| | | | | |
|---|---|---|---|---|
| 7,107,837 B2* | 9/2006 | Lauman et al. ............. 73/304 C | WO | 00/20052 | 4/2000 |
| 7,208,092 B2* | 4/2007 | Micheli .................. 210/646 | WO | 00/50143 | 4/2000 |
| 2001/0027289 A1 | 10/2001 | Treu et al. | WO | 00/57928 | 10/2000 |

FOREIGN PATENT DOCUMENTS

| | | |
|---|---|---|
| DE | 19814695 C2 | 9/2001 |
| EP | 64393 | 11/1982 |
| EP | 152717 | 8/1985 |
| EP | 0243547 B1 | 7/1991 |
| EP | 0402505 B1 | 12/1993 |
| EP | 0498382 B1 | 11/1996 |
| EP | 0778033 A2 | 11/1996 |
| EP | 0575512 B1 | 5/1998 |
| EP | 0847769 B1 | 6/1998 |
| EP | 0928615 A1 | 7/1999 |
| EP | 0956876 A1 | 11/1999 |
| EP | 980685 | 2/2000 |
| EP | 0659092 B1 | 10/2000 |
| EP | 1110565 A2 | 6/2001 |
| EP | 1121948 | 8/2001 |
| GB | 2122509 | 1/1984 |
| GB | 2124511 | 2/1984 |
| JP | 80-032384 | 8/1978 |
| JP | 55-045437 | 9/1978 |
| JP | 55-32384 | 3/1980 |
| JP | 92-002060 | 4/1990 |
| JP | 4-348757 | 12/1990 |
| JP | 07-299455 | 5/1994 |
| JP | 96-029224 | 7/1994 |
| JP | 80-29224 | 2/1996 |
| JP | 10-085324 | 9/1996 |
| JP | 11-137672 | 11/1997 |
| JP | 200120483 | 12/2000 |
| JP | 9-327511 | 6/2006 |
| SU | 1012918 | 12/1981 |
| SU | 1344362 | 6/1984 |
| WO | 94/20158 | 9/1994 |
| WO | 95/02559 | 1/1995 |
| WO | 95/35124 | 12/1995 |
| WO | 97/47337 | 12/1997 |
| WO | 98/17333 | 4/1998 |
| WO | 99/03519 | 1/1999 |
| WO | 99/06082 | 2/1999 |
| WO | 00/20050 | 4/2000 |

OTHER PUBLICATIONS

PCT/US03/22269 Search Report from corresponding PCT application, Mar. 26, 2004.

"Fresenius 90/2 Peritoneal Therapy Cycler" Article, written by Fresenius USA, dated Jul. 1993.

Roberts et al. Journal Publication, Innovative Peritoneal Analysis; Flow Thru and Dialysate Regeneration; Scholarly Review, ASA10 Journal, 1999, pp. 372-378.

Innovative Peritoneal Dialysis: Flow-Thru and Dialysate Regeneration, Asaio Journal, Lippincott Williams & Wilkins/Asaid, Hagerstwon, MD, US, vol. 45, No. 5, Sep. 1999, pp. 372-378, XP000880996, ISSN: 1058-2916.

Vychytil et al. "The role of tidal peritoneal dialysis in modern practice: a European perspective". Kidney International. 2006, vol. 70: S96-S103.

Ronco article entitled "Continuous Flow Peritoneal Dialysis: Is There a Need for it?" *Seminars in Dialysis*, vol. 14, No. 5, Sep.-Oct. 2001, pp. 395-400.

European Search Report/Search Opinion for Application No. EP 09 07 5523 dated Jun. 23, 2010.

Non-Final Office Action for U.S. Appl. No. 11/690,584 dated Aug. 7, 2007.

Final Office Action for U.S. Appl. No. 11/690,584 dated Nov. 20, 2007.

Non-Final Office Action for U.S. Appl. No. 11/690,584 dated Jun. 4, 2008.

Non-Final Office Action for U.S. Appl. No. 11/690,584 dated Mar. 27, 2009.

Final Office Action for U.S. Appl. No. 11/690,584 dated Oct. 28, 2009.

Non-Final Office Action for U.S. Appl. No. 12/562,737 dated May 28, 2010.

Final Office Action for U.S. Appl. No. 12/562,737 dated Sep. 20, 2010.

* cited by examiner

SYSTEMS AND METHODS FOR PERITONEAL DIALYSIS

PRIORITY CLAIM

This application is a continuation of U.S. patent application Ser. No. 11/690,584, filed on Mar. 23, 2007, now abandoned, which is a continuation of U.S. patent application Ser. No. 10/623,317, filed Jul. 17, 2003, now U.S. Pat. No. 7,208,092, and also claims the benefit of U.S. Provisional Patent Application No. 60/397,045, filed Jul. 19, 2002, all entitled "Systems And Methods For Peritoneal Dialysis"; the entire contents of which are hereby incorporated by reference and relied upon.

BACKGROUND OF THE INVENTION

The present invention generally relates to systems and methods for providing peritoneal dialysis. More specifically, the present invention relates to systems and methods for providing continuous flow peritoneal dialysis.

Due to disease, insult or other causes, a person's renal system can fail. In renal failure of any cause, there are several physiological derangements. The balance of water, minerals and the excretion of daily metabolic load is no longer possible in renal failure. During renal failure, toxic end products of nitrogen metabolism (e.g., urea, creatinine, uric acid, and others) can accumulate in blood and tissues.

Kidney failure and reduced kidney function have been treated with dialysis. Dialysis removes waste, toxins and excess water from the body that would otherwise have been removed by normal functioning kidneys. Dialysis treatment for replacement of kidney functions is critical to many people because the treatment is life saving. One who has failed kidneys could not continue to live without replacing at least the filtration functions of the kidneys.

Hemodialysis and peritoneal dialysis are two types of dialysis therapies commonly used to treat loss of kidney function. Hemodialysis treatment removes waste, toxins and excess water directly from the patient's blood. The patient is connected to a hemodialysis machine and the patient's blood is pumped through the machine. For example, needles or catheters can be inserted into the patient's veins and arteries to connect the blood flow to and from the hemodialysis machine. As blood passes through a dialyzer in the hemodialysis machine, the dialyzer removes the waste, toxins and excess water from the patient's blood and returns the blood to infuse back into the patient. A large amount of dialysate, for example about 90-120 liters, is used by most hemodialysis machines to dialyze the blood during a single hemodialysis therapy. The spent dialysate is then discarded. Hemodialysis treatment lasts several hours and is generally performed in a treatment center about three times per week.

Another type of hemodialysis therapy is regenerative hemodialysis. This therapy uses a hemodialysis system, which includes a cartridge for dialysate regeneration. One such cartridge is manufactured under the name REDY™ by Sorb Technology, Oklahoma City, Okla. In this system, the dialysate fluid flow path must be properly cleaned before the hemodialysis machine can be used on another patient. Also, the dialysate fluid flow path is not a closed system. In this regard, the dialysate fluid flow path is open to the atmosphere such that air borne pathogens can contact the fluid in the system and foster the growth of bacteria in same. Consequently, contamination of such a dialysis system can be problematic. Thus, the dialysate fluid exiting the REDY™ cartridge is not suitable for peritoneal dialysis.

Peritoneal dialysis utilizes a sterile dialysis solution or "dialysate", which is infused into a patient's peritoneal cavity and into contact with the patient's peritoneal membrane. Waste, toxins and excess water pass from the patient's bloodstream through the peritoneal membrane and into the dialysate. The transfer of waste, toxins, and excess water from the bloodstream into the dialysate occurs due to diffusion and osmosis during a dwell period as an osmotic agent in the dialysate creates an osmotic gradient across the membrane. The spent dialysate is later drained from the patient's peritoneal cavity to remove the waste, toxins and excess water from the patient.

There are various types of peritoneal dialysis therapies, including continuous ambulatory peritoneal dialysis ("CAPD") and automated peritoneal dialysis. CAPD is a manual dialysis treatment, in which the patient connects the catheter to a bag of fresh dialysate and manually infuses fresh dialysate through the catheter and into the patient's peritoneal cavity. The patient disconnects the catheter from the fresh dialysate bag and allows the dialysate to dwell within the cavity to transfer waste, toxins and excess water from the patient's bloodstream to the dialysate solution. After a dwell period, the patient drains the spent dialysate and then repeats the manual dialysis procedure. Tubing sets with "Y" connectors for the solution and drain bags are available that can reduce the number of connections the patient must make. The tubing sets can include pre-attached bags including, for example, an empty bag and a bag filled with dialysate.

In CAPD the patient performs several drain, fill, and dwell cycles during the day, for example, about four times per day. Each treatment cycle, which includes a drain, fill and dwell, takes about four hours. Manual peritoneal dialysis performed by the patient requires a significant amount of time and effort from the patient. This procedure leaves room for improvement and therapy enhancements to improve patient quality of life.

Automated peritoneal dialysis is similar to continuous ambulatory peritoneal dialysis in that the dialysis treatment includes a drain, fill, and dwell cycle. However, a dialysis machine automatically performs three or more cycles of peritoneal dialysis treatment, typically overnight while the patient sleeps.

With automated peritoneal dialysis, an automated dialysis machine fluidly connects to an implanted catheter. The automated dialysis machine also fluidly connects to a source or bag of fresh dialysate and to a fluid drain. The dialysis machine pumps spent dialysate from the peritoneal cavity, through the catheter, to the drain. The dialysis machine then pumps fresh dialysate from the dialysate source, through the catheter, and into the patient's peritoneal cavity. The automated machine allows the dialysate to dwell within the cavity so that the transfer of waste, toxins and excess water from the patient's bloodstream to the dialysate solution can take place. A computer controls the automated dialysis machine so that the dialysis treatment occurs automatically when the patient is connected to the dialysis machine, for example, when the patient sleeps. That is, the dialysis system automatically and sequentially pumps fluid into the peritoneal cavity, allows for dwell, pumps fluid out of the peritoneal cavity, and repeats the procedure.

Several drain, fill, and dwell cycles will occur during the treatment. Also, a smaller volume "last fill" is typically used at the end of the automated dialysis treatment, which remains in the peritoneal cavity of the patient when the patient disconnects from the dialysis machine for the day. Automated peritoneal dialysis frees the patient from having to manually perform the drain, dwell, and fill steps during the day. Automated dialysis can improve the patient's dialysis treatment and undoubtedly improves the patient's quality of life, as compared to CAPD.

"Continuous flow" peritoneal dialysis ("CFPD") systems have been contemplated since the 1970's. These systems typically have an in fluid flow and an out fluid flow. That is, the dialysate flows in one catheter lumen, through the peritoneum and out another catheter lumen to the drain line. The "spent" dialysate (waste laden dialysate) collects in a drain bag, which is discarded, or is fed into a household or other drain. Known CFPD systems typically use a volume of dialysate one time and then discard it. In this regard, the volume of dialysate necessary to carry out treatment for a continuous flow single use or pass system can be large in size rendering their daily use cost prohibitive. For example, the volume of dialysate can exceed 120 liters for single pass CFPD systems.

Another type of a CFPD system is disclosed in U.S. Pat. No. 3,707,967. This system requires the use of a reconstitution device to remove waste from the dialysate after the dialysate has passed through the patient's peritoneum. In particular, the reconstitution device includes a urea removal column that employs urease to enzymatically convert urea into ammonia. The ammonia must then be removed from the dialysate prior to reintroduction into the peritoneal cavity in order to ensure the health and safety of the patient. However, the removal of ammonia can be problematic and thus may not provide a failsafe measure. Moreover, additional sensors must be employed to monitor the removal of ammonia from the reconstituted dialysate. This can add to the complexity of the therapy and thus increase the cost associated with same.

In general, CFPD is known to be more effective as compared to other forms of peritoneal dialysis therapy including, for example, more conventional forms of peritoneal dialysis therapies, such as CAPD and APD which typically require multiple exchanges of fresh dialysate during treatment. As previously discussed, several drain, fill and dwell cycles are typically performed during CAPD and APD. An example of a modification of the more conventional forms of peritoneal dialysis therapy is disclosed in U.S. Pat. No. 4,618,343. An apparatus is disclosed that allows the peritoneal cavity of the patient to be filled with a sterile dialysis liquid as in the case of CAPD. After a dwell period, the dialysis liquid retains metabolic waste from the patient's blood. A portion of the dialysis liquid containing the metabolic waste is then pumped out of the peritoneal cavity and passed through a dialyzer to remove the metabolic waste from the dialysis liquid. The dialysis liquid can then be pumped back into the peritoneal cavity for reuse.

Therefore, a need exists to provide improved dialysis systems. The systems should allow the patient to perform the procedure at home without the need for storing an inordinate amount of fresh dialysate bags. The systems should further be automated so that the procedure can be largely performed at night while the patient sleeps.

SUMMARY OF THE INVENTION

The present invention relates to systems and methods for providing peritoneal dialysis. In particular, the present invention relates to continuous flow peritoneal dialysis that employs a single closed fluid path along which dialysate can be circulated into, through and out of a peritoneal cavity of a patient in order to effectively remove acceptable levels of solutes and excess water or ultrafiltrate from the patient during treatment.

In general, the present invention includes a fluid circuit which is coupled to the patient thereby defining a single closed fluid path along which the dialysate can be circulated and thus reused during the entire treatment. Preferably, the dialysate is circulated along the fluid path in a continuous manner. In this regard, the amount of dialysate necessary for effective treatment can be optimally minimized. In an embodiment, the present invention can utilize six liters or less of dialysate during treatment. With this amount of reusable dialysate, effective treatment can be conducted over periods of at most 10 hours, preferably about 8 hours or less, more preferably about 7 hours or less.

Prior to reuse, the dialysate is cleaned as it circulates along the closed fluid path. In an embodiment, the present invention includes a cleaning device which is coupled to the closed fluid path. The cleaning device is capable of removing an acceptable level of solutes including uremic toxins or other metabolic waste products that have passed from the patient to the dialysate during treatment. The amount of solutes removed from the dialysate is necessary to maintain a diffusive gradient at a sufficient level such that solutes and ultrafiltrate can be effectively removed from the patient upon reuse of the dialysate during treatment.

In this regard, it is believed that the dialysate does not necessarily have to be cleaned or regenerated to its initial fresh state prior to reuse. Rather, the dialysate, after cleaning, may retain some concentration of solutes removed from the patient, particularly urea. In an embodiment, the cleaning device employs a sorbent material, such as carbon, to non-selectively remove a substantial portion of solutes from the dialysate. This can include, for example, toxins removed from the patient, such as creatinine, uric acid, mid-range molecular weight constituents, at least a portion of urea and other like low molecular weight constituents and the like. Preferably, the cleaning device includes a binder material to selectively remove urea, phosphate and/or other like solutes.

Even after cleaning, if the dialysate retains, for example, a portion of urea removed from the patient, it is believed that the dialysate can be circulated along the closed fluid path to remove solutes from the patient at or exceeding therapy level standards, such as DOQI standards. It is believed that the available volume of therapy fluid including dialysate can be controllably minimized, circulated and cleaned during the entire treatment to achieve clinically acceptable levels of solute clearance. Further, it is believed that the systems and methods of the present invention can achieve better clearance levels as compared to known therapies including, for example, APD.

The available volume therapy fluid can be influenced by a number of factors, such as the amount dialysate fed into the closed fluid path, the amount of ultrafiltrate added to the closed fluid path and the amount of additional other solutions that can be added to the closed fluid path to enhance the diffusive properties of the dialysate. In an embodiment, the therapy volume is controllably adjusted by the amount of dialysate that is fed into the closed fluid path in addition to the ultrafiltrate that passes from the patient into the closed fluid path during treatment. To compensate for the amount of ultrafiltrate, the volume capacity of the closed fluid path can be variably adjusted during treatment. In this regard, the addition of ultrafiltrate to the fluid circuit, in effect, increases the capacity to remove solutes by keeping the additional volume in contact with the loop. In an embodiment, about 1.5 liters or less of ultrafiltrate is utilized during therapy.

Additional other solutions can be added to the closed fluid path in controlled amounts to further enhance the effectiveness of solute removal during therapy. In an embodiment, a solution that contains an osmotic agent, such as dextrose, can be added to the closed fluid path in addition to the initial source of dialysate and the added source of ultrafiltrate. Preferably, about 3 liters or less of the additional osmotic agent solution is added. The dextrose-based solution can be utilized to replenish the diffusive properties of the dialysate prior to reuse. In an embodiment, the dextrose-based solution contains a concentrated amount of dextrose as compared to the amount of dextrose or other osmotic agent in the initial source of dialysate.

Further, it is believed that the available amount of therapy fluid necessary for effective treatment can be minimized with increased cleaning efficiency. In an embodiment, the present invention can utilize, in addition to carbon, binder or reactive materials which are capable of selectively removing specific types of solutes from the dialysate as previously discussed. The binder materials can be utilized to remove urea, phosphates or other desirable metabolic waste products that may be retained in the dialysate even after carbon treatment. Preferably, the combination of non-selective and selective cleaning agents can be utilized to remove up to about 70% or greater of urea and other like constituents from the dialysate.

An advantage of the present invention is to provide improved systems and methods for providing dialysis therapy.

Another advantage of the present invention is to provide improved systems and methods for continuous flow peritoneal dialysis.

Yet another advantage of the present invention is to provide an optimal use of dialysate during continuous flow peritoneal dialysis.

Yet still another advantage of the present invention is to minimize treatment times while providing optimal use of the dialysate during continuous flow peritoneal dialysis.

A further advantage of the present invention is to provide improved systems and methods for performing dialysis therapy which can be safely and conveniently administered to a patient in a home setting.

Yet a further advantage of the present invention is to provide improved systems and methods of peritoneal dialysis that can effectively clean spent dialysate such that it can be circulated and reused during treatment in order to minimize the amount of dialysate necessary for effective treatment.

Additional features and advantages of the present invention are described in, and will be apparent from, the following Detailed Description of the Invention and the Figures.

DETAILED DESCRIPTION OF THE INVENTION

Figure 1:
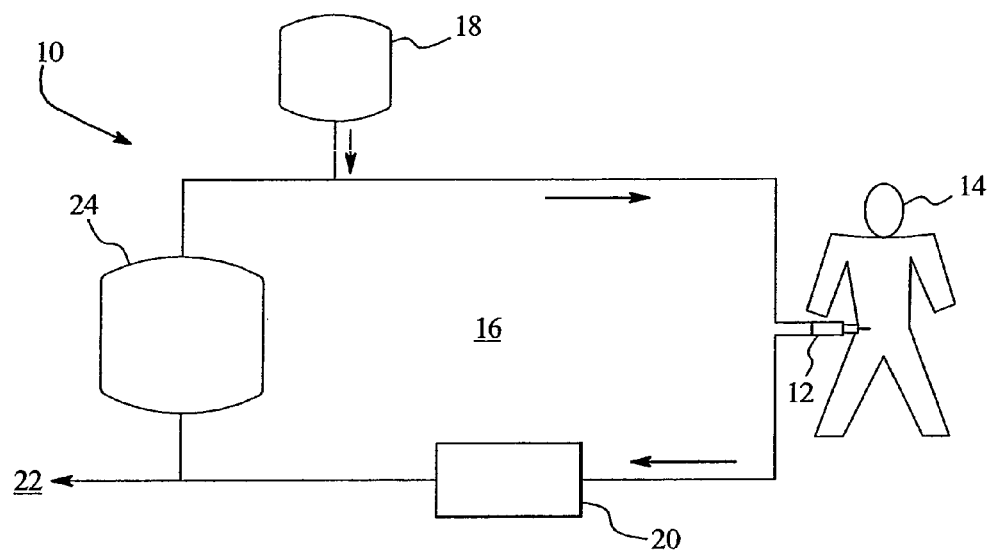
FIG. 1 schematically illustrates a dialysis system according to an embodiment of the present invention.

In general, the present invention employs a single closed fluid path along which a minimal volume of therapy fluid can be circulated such that the therapy fluid can pass into, through and out of a peritoneal cavity of a patient connected to the closed fluid path to effectively remove solutes, excess water and the like from the patient during treatment. In an embodiment, the available volume of therapy fluid can include about 6 liters or less of an initial source of dialysate. It is believed that the available volume of therapy fluid can be circulated along the closed fluid path to remove solutes from the patient at or exceeding clinically acceptable solute removal standards, such as the National Kidney Foundation's DOQI levels. In an embodiment, acceptable solute removal or clearance levels can be achieved over a period of 8 hours or less, preferably 7 hours or less, during treatment.

For example, it is believed that a therapeutic level of clearances can be achieved for urea, creatinine, phosphate, β2 microglobulin, the like and combinations thereof. The clearance levels can include, for example, about 2.1 per week to about 2.6 per week for urea; about 72 liters (l)/week (wk) to about 90 l/wk for creatinine; about 3.5 grams (g)/week (wk) for phosphate; about 600 milligrams (mg)/week (wk) for β2 microglobulin, the like and combinations thereof. It should be appreciated that the clearance levels can be determined in any suitable way. For example, the urea clearance levels can be based on Kt/V calculations. In this regard, Kt/V is generally recognized in the art as a dimensionless index that corresponds to urea clearance.

As used herein, the term "continuous flow" or other like terms as applied to dialysis therapy, such as peritoneal dialysis, means that the therapy fluid including dialysate is constantly and simultaneously flowing into and out of the patient's peritoneum during treatment. In this regard, the dwell period of the dialysate inside the peritoneum associated with typical peritoneal dialysis therapies, such as CAPD and APD, is effectively eliminated.

Preferably, the therapy fluid is circulated in a continuous manner during treatment. However, it should be appreciated that fluid flow of the present invention can include any suitable level of intermittent, non-continuous batch, tidal and/or other like fluid flow in addition to continuous flow during treatment. For example, the present invention may provide for brief intermittent fluid flow, such as during the filling of a pump chamber, the fluid loop, the patient and/or the like prior to treatment, brief periods of downtime or breaks in therapy and/or other like suitable conditions. In this regard, the present invention can be controlled to provide a variety and number of suitable dialysis therapies, as desired. In an embodiment, the continuous flow into, through and out of the peritoneal cavity preferably occurs during the main therapy treatment, so that a dwell during a last bag, for example, does not detract from the continuous flow feature.

As used herein, the term "therapy fluid" or other like terms means any suitable fluid or solution that can be used during dialysis therapy. The therapy fluids can include, for example, a fresh source of dialysate solution that has not been used during therapy, a waste laden dialysate that contains solutes, metabolic waste and the like removed from the patient during therapy, a clean source of dialysate that has been cleaned by sorbent materials or the like, a source of ultrafiltrate that has been passed from the patient to be mixed with the dialysate during treatment, a solution that includes an osmotic agent in a sufficient amount to enhance the diffusive properties of the dialysate when added to the dialysate, other suitable solutions and combinations thereof.

In general, the present invention includes a fluid circuit which is coupled to the patient thereby defining the single closed fluid path into which an effective amount of a fresh source of dialysate can be initially added. The dialysate can then be circulated, preferably in a continuous manner, and cleaned along the closed fluid path and thus continually reused to remove solutes, excess water and the like from the patient.

It is believed that the dialysate does not necessarily have to be cleaned or regenerated to its original fresh state prior to reuse. Rather, the dialysate, after cleaning, may retain some concentration of solutes that was removed from the patient during therapy. This is particularly relevant to the removal of urea or other like solutes.

In this regard, urea is typically removed by employing an enzymatic process that converts urea into by-products, such as ammonia. The by-products can then be removed. However, from a patient health and safety perspective, this type of cleaning process would necessarily require additional components, such as sensors or the like, to ensure that the by-products, particularly ammonia, have been effectively removed prior to recirculation into, through and out of the patient. Even if urea or other like solutes are not completely removed from the dialysate or removed to typically acceptable levels prior to reuse, it is believed that effective and clinically acceptable levels of solute removal can be achieved upon reuse of the dialysate during treatment.

To compensate for the concentration of solutes that may be retained in the dialysate prior to reuse, the present invention can controllably minimize, circulate and clean the available volume of therapy fluid during the entire treatment. The available volume of therapy fluid can be controllably adjusted based on a number of parameters, such as the amount of initial source of dialysate pumped into the closed fluid path, the amount of ultrafiltrate added to the closed fluid path, the amount of additional other solutions that include osmotic agents and/or other suitable constituents to enhance the diffusive properties of the dialysate, and other like parameters as described in detail below.

The available volume of therapy fluid necessary for effective treatment can also be influenced by the efficiency of the cleaning process. As described below, carbon or other like materials can be utilized to clean the dialysate as it circulates along the closed fluid path. The cleaning efficiency can be increased with the use of materials that can selectively remove solutes in combination with the non-selective removal capabilities of carbon or other like materials. This can be performed without the use of an enzymatic conversion process that produces reaction by-products, such as the conversion of urea into ammonia, thus effectively eliminating the need to remove the by-products from the solution prior to reuse.

The dialysis systems and methods of the present invention provide advantages, it is believed, compared to existing dialysis systems and therapies, such as clinical advantages, economic advantages, and quality of life advantages, for example. It is believed that the present invention has clinical advantages, such as, improved blood pressure control, improved fluid volume control, improved therapy performance as assessed by known clinical standards, such as the National Kidney Foundation's DOQI standard, higher clearance efficiency rates, lower glucose absorption, glucose profiling and ultrafiltrate management, reduced catheter channeling and/or the like.

It is also believed that the present invention provides economic advantages, such as, reduced therapy cost. Further, it is believed that present invention has quality of life advantages, such as, increased awake time free from dialysis devices, improved patient access, reduced complexity, reduced self-administration of drugs, reduced therapy training, elimination of the need for having a home water infrastructure, a reduced amount of fluid that the patient must handle and manage, simpler prescriptions, elimination of patient transportation to dialysis centers and/or the like.

It is believed that the continuous flow dialysis systems and methods of the present invention more closely simulate and replace continuous kidney functioning as compared to typical intermittent dialysis therapies. This, in turn, can contribute to improved clinical outcomes while minimally impacting the patient's lifestyle. The efficiency and convenience of the present invention provides patients with a renal replacement therapy that is relatively unrestrictive. This allows patients to have greater freedom from limitations experienced by conventional dialysis devices and therapies. The present invention can provide easier entrance into early dialysis therapy because the system can enable the physician to monitor therapy while minimally impacting the patient's lifestyle.

The continuous flow peritoneal dialysis therapy of the present invention can include a variety of different components and configurations to effectively remove solutes from the patient with a minimal volume of therapy fluid and within an optimal time frame as previously discussed. As shown in FIG. 1, the present invention includes a fluid circuit 10 in fluid communication with a catheter 12 insertable within a patient 14 undergoing peritoneal dialysis. This defines a single closed fluid path 16 along which dialysate can be fed into and circulated, preferably in a continuous manner, to remove excess water and solutes including toxins and metabolic waste and the like from the patient as the dialysate passes into, through and out of the peritoneal cavity of the patient.

Catheter

Any suitable catheter or other medically acceptable access device can be utilized. In a preferred embodiment, a dual lumen catheter can be used. The dual lumen catheter provides for circulation of the therapy fluid along the fluid path allowing flow into, through and out of the peritoneal cavity of the patient. To this end, the dual lumen catheter is implanted in the patient. An example of a catheter for use in the dialysis system of the present invention is disclosed in U.S. patent application Ser. No. 09/689,508, filed on Oct. 12, 2000, now U.S. Pat. No. 6,976,973, and entitled "Peritoneal Dialysis Catheter," the disclosure of which is incorporated herein by reference. However, it should be noted that two single lumen catheters can be used as long as there is an inflow and outflow path for circulation of fluid through the peritoneum.

Dialysate

The fresh or initial source of dialysate can include any suitable amount and type of solution that can be effectively used to dialyze a patient. As previously discussed, the present invention can meet and/or exceed clinically acceptable solute removal levels while utilizing a minimal volume of therapy fluid. In an embodiment, the volume of dialysate used during therapy is about 6 liters or less. It is believed that the lower range limit of the volume of dialysate can reach volume levels as low as about 5 liters or even lower as the cleaning efficiency of the dialysate in circulation along the closed fluid path is increased.

The dialysate solution can be fed into the closed fluid path in a variety of suitable ways. In an embodiment, the entire volume of the fresh source of dialysate is fed into the closed fluid loop at the beginning of therapy. This can be performed by any suitable pumping mechanism. The entire volume can be contained in and fed from one or more suitable solution containers 18, such as conventional dialysis solution bags that are about 6 liters in capacity. Alternatively, the dialysate can be generated and fed from an on-line dialysate generation system. In an embodiment, the dialysate can be intermittently and/or continuously fed into closed fluid path during the entire therapy at any suitable flow rates and/or amounts.

The dialysate solution can include any suitable type of dialysate solution. In an embodiment, the fresh source of dialysate solution includes an osmotic agent, such as dextrose or the like in any suitable amount. It should be appreciated that the amount of dextrose necessary for effective therapy may vary from patient to patient. In this regard, the amount of osmotic agent can vary and include any clinically acceptable level, such as about 1.5% by weight, about 2.5% by weight, about 3.5% by weight, about 4.25% by weight or greater to meet the specific needs of the patient. The dialysate can include any suitable amount and type of electrolytes in addition to the osmotic agent including, for example, calcium, sodium, potassium, like constituents and combinations thereof.

Cartridge

As shown in FIG. 1, the present invention can include any suitable type of device 20 which utilizes any suitable amount and type of material to effectively clean the therapy fluid as it circulates along the closed fluid path. This facilitates the reuse of the therapy fluid to remove effective levels of solutes, excess water and the like from the patient during therapy. In an embodiment, the cleaning device includes a material that is capable of non-selective removal of solutes from the therapy fluid that have been removed from the patient during therapy. Preferably, the material includes any suitable sorbent material, such as carbon, activated carbon and/or other like material that is contained within a suitable housing, such as a cartridge, in any acceptable manner. As previously discussed, it is believed that the non-selective removal of solutes from the dialysate can be used, on its own, to clean the dialysate such that effective removal of solutes and excess water from the patient can occur upon reuse of the dialysate.

In an embodiment, the present invention can include other materials in addition to those types of materials which can non-selectively remove solutes from the dialysate. The additional other materials include, for example, materials that can selectively remove certain solutes or the like from solution. In an embodiment, the additional materials include a binder material capable of selectively removing urea, a binder material capable of selectively removing phosphate and/or the like.

In general, the binder materials chemically bind the solutes, such as urea, to remove them from the dialysate or other suitable fluid medium as described below in greater detail. This process does not result in the release of harmful substances as reaction by-products as compared to an enzymatic process. For example, urease is known to enzymatically convert urea into ammonia. However, ammonia must then be removed from the dialysate prior to reintroduction into the peritoneal cavity in order to ensure the health and safety of the patient. With the use of binder materials, the dialysate can be reintroduced into the peritoneal cavity without further processing of the dialysate as a result of the binder process. As previously discussed, the use of materials capable of selective removal of solutes, particularly urea, can be used to enhance the cleaning efficiency of the system of the present invention such that less therapy volume would be needed to provide effective therapy.

The materials that can selectively remove solutes from solution, such as binder materials, can include a variety of suitable and different materials including, for example, polymeric materials that are capable of removing nitrogen-containing compounds, such as urea, creatinine, other like metabolic waste and/or the like in solution. In general, these types of materials contain a functional group(s) that chemically binds with urea or other like solutes.

For example, U.S. Pat. Nos. 3,933,753 and 4,012,317, each incorporated herein by reference, disclose alkenylaromatic polymers containing phenylglyoxal that can function to chemically bind urea. In general, the phenylglyoxal polymeric material is made via acetylation performed in, for example, nitrobenzene followed by halogenation of the acetyl group and treatment with dimethylsulfoxide as disclosed in U.S. Pat. Nos. 3,933,753 and 4,012,317. Another example of a polymeric material that is capable of selectively removing solutes, such as urea, from solution includes polymeric materials that contain a tricarbonyl functionality commonly known as ninhydrin as disclosed in U.S. Pat. No. 4,897,200, incorporated herein by reference. However, it should be appreciated that the present invention can include any suitable type of material or combinations thereof to selectively remove solutes, such as urea, from solution as previously discussed.

The cleaning cartridge of the present invention can include a number of components in addition to the materials capable of removing solutes from the dialysate. For example, the cleaning cartridge may have the capability to remove all or a portion of electrolytes, such as sodium, potassium, or the like, from the dialysate solution. In this case, an additional source of electrolytes in solution may be needed to replenish the dialysate after it has been cleaned. The cartridge may also be configured to release bicarbonate or the like into the system depending on the type of cleaning material used. This can facilitate pH regulation of the dialysate. As necessary, the cartridge may include a filter to prevent proteins, particulate matter or like constituents from leaching or exiting from the cartridge and into the dialysate.

Treatment Conditions

During treatment, the therapy fluid, including the dialysate, is circulated, preferably in a continuous manner, and cleaned along the closed fluid path such that it can be continually reused to provide effective treatment of the patient. The therapy fluid can be circulated at any acceptable flow rate. In an embodiment, the fluid flow rate in the closed fluid loop can be varied up to about 300 ml/min, preferably about 100 ml/min or less. At these flow rates, the present invention can provide effective treatment to the patient in 8 hours or less, preferably 7 hours or less. In an embodiment, the systems and methods of the present invention are conducted during the night. Preferably, the treatment therapy of the present invention is combined with an all day dwell period where a suitable amount of dialysate has dwelled within the patient. In an embodiment, the all day dwell includes about 2 liters or less of dialysate. It should be appreciated that this volume can vary from patient to patient depending on the specific needs of the patient.

The peritoneal dialysis of the present invention can be performed in a variety of suitable manners. In an embodiment, the entire volume of the fresh source of dialysate is fed into the fluid circuit at the beginning of the treatment. In this regard, the peritoneal cavity of the patient is filled with about 3 liters of the fresh source of dialysate solution and the remaining portion of the dialysate is pumped into the fluid circuit before the dialysate is circulated during treatment. It should be appreciated that the initial fill volume of dialysate within the patient's peritoneal cavity may vary from patient to patient.

Alternatively, the treatment period can be performed over a number of treatment cycles. In an embodiment, the treatment period can include two separate treatment cycles. In each cycle, about any suitable portion of the fresh source of dialysate is initially fed into the fluid circuit and then circulated for an effective treatment cycle period of about 4 hours or less. After the first cycle, the entire volume of therapy fluid including the dialysate in addition to any amount of ultrafiltrate or additional solutions that were added to the fluid circuit during treatment is drained from the fluid circuit. Once drained, the remaining portion of fresh dialysate is fed into the fluid circuit and circulated until treatment is complete.

Cycler

In an embodiment, the fresh source of dialysate can be pumped into and circulated along the fluid circuit and drained from the fluid circuit after each treatment cycle with the use of a device which is commonly known in the art as a cycler (not shown). As used herein, the term "cycler" or other like terms refers to a pressure driven, diaphragm-type volumetric displacement pump coupled to a fluid path or paths in any suitable manner such that fluid flow can be automatically controlled. The cycler can determine the volume of liquid delivered as the difference in the volume of a pumping chamber before and after a pumping stroke. The pumping chamber, in general, includes two parts separated by a flexible diaphragm with air on one side and fluid on the other. Increasing the air pressure pushes liquid out of the chamber expanding the volume on the air side.

It should be appreciated that the cycler can include any suitable number and types of components, such as pumps and valves, coupled to any suitably designed fluid circuit to provide efficient and effective automatic control of therapy fluid flowing into and out of the closed fluid path 16. For example, the cyclers typically applied during automated peritoneal dialysis and suitable modifications thereof can be employed.

Examples of a cycler are disclosed in U.S. Patent Applications: "Peritoneal Dialysis Systems and Methods Employing a Liquid Distribution and Pumping Cassette That Emulates Gravity Flow," filed Mar. 3, 1993, Ser. No. 08/027,328, issued as U.S. Pat. No. 5,350,357; "Liquid Pumping Mechanisms for Peritoneal Dialysis Systems Employing Fluid Pressure," filed Mar. 3, 1993, Ser. No. 08/027,485, issued U.S. Pat. No. 5,431,626; "Peritoneal Dialysis Systems and Methods Employing Pneumatic Pressure and Temperature-Corrected Liquid Volume Measurements," filed on Mar. 3, 1993, Ser. No. 08/026,458, issued as U.S. Pat. No. 5,474,683; "Improved User Interface and Monitoring Functions for Automated Peritoneal Dialysis," filed Mar. 3, 1993, Ser. No. 08/025,531, issued as U.S. Pat. No. 5,438,510; "Improved User Interface for Automated Peritoneal Dialysis Systems," filed Mar. 3, 1993, Ser. No. 08/025,547, issued as U.S. Pat. No. 5,324,422; and "Peritoneal Dialysis Cycler," filed Mar. 3, 1993, Ser. No. 08/006,426, issued as U.S. Pat. No. D 351,470, the disclosures of all of which are incorporated herein by reference. It should be appreciated that the cycler can be coupled to the continuous flow system in any suitable manner, such as with the use of any suitable disposable cartridge that can be used as a fluid interface between the patient and the fluid circuit to readily and easily couple the patient to the fluid circuit as typically employed during automated peritoneal dialysis and/or modifications thereof.

After treatment, the therapy fluid is removed from the fluid circuit through a discharge path 22 which is coupled to the fluid circuit. The therapy fluid can be discharged in any suitable manner, such as by any suitable pump mechanism coupled to the fluid discharge path. The discharged therapy fluid can be disposed of or alternatively can be regenerated for prior use.

Additional Osmotic Agent

Figure 2:
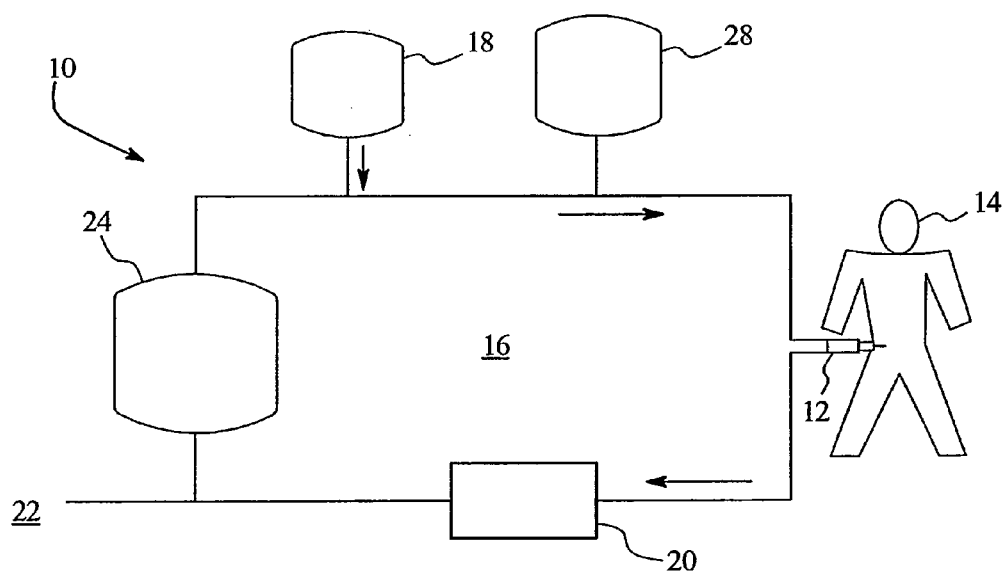
FIG. 2 schematically illustrates a dialysis system according to another embodiment of the present invention.

Referring now to FIG. 2, the present invention can include a source of fluid 28 in addition to the dialysate and the ultrafiltrate which can be added to the fluid circuit during treatment. The additional fluid source can include one or more solutions, such as an aqueous solution that contains an osmotic agent, such as dextrose or the like, in a sufficient amount in order to replenish the diffusive properties of the therapy fluid during treatment. The amount of osmotic agent can include about 2.5% by weight, about 3.5% by weight, about 4.25% or greater by weight of the suitable amounts and combinations thereof. The additional solution source can also include an acceptable level and type of other constituents, such as electrolytes including calcium, magnesium, sodium, the like and combinations thereof, in addition to the osmotic agent. In an embodiment, the amount of osmotic agent solution added to the fluid circuit is about 3 liters or less, preferably about 2 liters or less. The osmotic agent solution can be continuously fed or intermittently fed into the closed fluid path on a monitored basis in any suitable manner.

It should be appreciated that the amount and type of osmotic agent solution necessary to facilitate effective treatment can vary from patient to patient. In an embodiment, a solution with a relatively high level of osmotic agent and electrolytes as compared to the existing therapy fluid can be fed to the fluid circuit in volumetric amounts of about 1 liter or less. In an embodiment, the solution concentrate of osmotic agent and electrolytes can include an osmotic agent, such as dextrose, at about 4.25% or greater by weight and concentration levels of electrolytes that are higher than existing levels in the therapy solution such that levels in the therapy solution can be adjusted to achieve optimal and physiological acceptable levels prior to reuse.

In an embodiment, components of the solution concentrate can be individually infused into the fluid circuit. The components can include those types of constituents typically contained in dialysate solutions including, for example, an osmotic agent, such as dextrose, bicarbonate, sodium, calcium, magnesium, like constituents and combinations thereof. The amount of individual components fed into the fluid circuit can be regulated and controlled in any suitable manner.

For example, a sensing device (not shown) can be coupled to the system of the present invention which can be utilized to provide on-line and real-time monitoring of the specific levels of the components during treatment. The sensor can then be configured to communicate with the infusion device (not shown) of each of the components to regulate the flow of components into the fluid circuit. This can also be utilized to monitor the level of ultrafiltrate removed from the patient. If more ultrafiltrate is desired, the sensor can be adapted to communicate with a pump to increase the flow of dextrose and thus, increase ultrafiltrate removal from the patient. In an embodiment, the amount of the individual components added during therapy can be regulated based on customized therapy profiles associated with each of the components.

In an embodiment, the available volume of therapy solution can include the initial amount of fresh dialysate, the amount of ultrafiltrate and/or other additional solutions, such as the dextrose-based solutions as previously discussed. Instead of variably increasing the volume capacity of the fluid circuit, the fluid circuit volume capacity can remain relatively constant during treatment. In this regard, an amount of therapy fluid is discharged from the fluid circuit at a rate approximate to the infusion of the dextrose-based solution and transport of ultrafiltrate into the fluid circuit. Preferably, the fluid circuit volume capacity can be fixed in this way as the cleaning efficiency of the therapy solution is increased. In this regard, a variable increase in the available volume of therapy fluid is not necessary for effective treatment.

Reservoir

In an embodiment, the present invention includes a reservoir 24 which is coupled to the fluid circuit. This can provide a variable increase in volume capacity of the fluid circuit during treatment. In this regard, the ultrafiltrate which passes from the patient and into the fluid circuit can be mixed with the dialysate and thus increase the volume of therapy fluid available for effective treatment.

As previously discussed, the addition of ultrafiltrate to the dialysate, in effect, increases the capacity to remove solutes by keeping the additional volume in contact with the fluid loop. This can facilitate the cleaning process and thus effectively minimize the volume of fresh dialysate that is necessary for treatment purposes. As used herein, the term "ultrafiltrate" or other like terms means the excess water that is removed from the patient as the dialysate acts to dialyze the patient. It should be appreciated that the reservoir can include any suitable components, such as any suitable container coupled to a pump which can act to variably increase the volume of the fluid circuit in any suitable manner. The container can include any suitable type of container such that a portion of fluid from the fluid loop can be effectively pumped into and out the container during therapy. Preferably, the accumulator container is not flexible. In this regard, fluid pumped into the fluid loop is designed to be pushed by pumps. Therefore, it would be difficult to control or regulate flow rates through the fluid circuit with a flexible container acting as an accumulator or variable reservoir.

Figure 3:
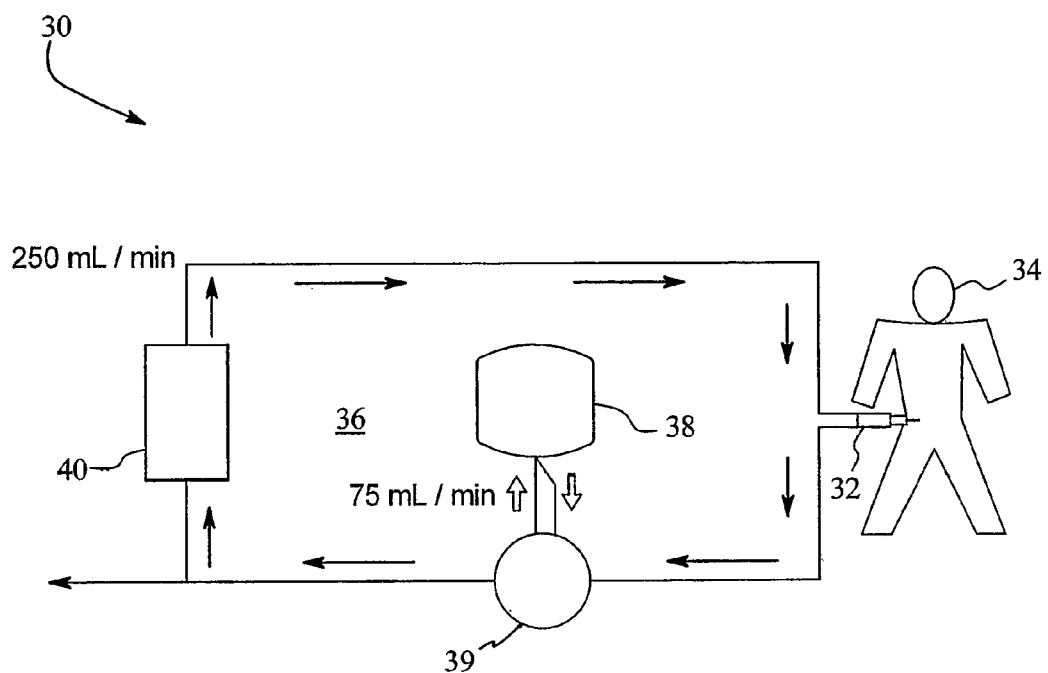
FIG. 3 schematically illustrates a dialysis system according to a further embodiment of the present invention.

As shown in FIG. 3, the present invention includes a fluid circuit 30 in fluid communication with a catheter 32 insertable within a patient 34 undergoing peritoneal dialysis. A single closed fluid path 36 is thereby defined. A source of dialysate is provided in a container 38 coupled to the fluid circuit 30. From the container, the dialysate can be pumped into and circulated along the fluid circuit to remove metabolic waste and/or ultrafiltrate from the patient as it passes into, through and out of the patient. A cleaning device 40 can also be coupled to the fluid circuit to clean the dialysate as it circulates along the fluid circuit 30 as previously discussed.

At the beginning of therapy, at least a portion of the dialysate is pumped into the fluid circuit 30 to fill the peritoneal cavity of the patient. The remaining portion, if any, of the dialysate can be pumped into the fluid circuit at a later stage in the therapy. As the therapy continues, a portion of the therapy fluid that has circulated along the fluid circuit can be pumped into the container 38 as the volume in therapy fluid increases due to, for example, the addition of ultrafiltrate to the fluid circuit that has been removed from the patient and/or an additional amount of osmotic agent solution (not shown) added to the fluid circuit 30 as previously discussed. At least a portion of the container 38 can be filled with the therapy fluid in a continuous manner or intermittently. At least a portion of the therapy fluid in the container 38 can be subsequently pumped back into the fluid circuit 30. Any suitable amount of therapy fluid can be sent to or pulled from the container at any suitable time intervals to adjust the volume of available therapy fluid. This allows the portion of therapy fluid to be pumped into or out the container while the remaining portion of the therapy fluid in the fluid circuit 30 continues to circulate along the fluid circuit 30.

It should be appreciated that any suitable volume of therapy fluid can be pumped into or out of the container to compensate for a change in volume of therapy fluid during therapy. The fluid flow into or out of the container 38 and in circulation along the fluid circuit can be controlled at any suitable flow rates and by any suitable type and number of pumps 39. The pumps can be coupled to the system via a cycler or one or more of the pumps can be separately coupled to the system. In an embodiment, the flow of fluid into or out of the container can be controlled at a flow rate of about 75 ml/min while the flow of fluid circulating along the fluid circuit can be controlled at about 250 ml/min as shown in FIG. 3.

It should be appreciated that the systems and methods of the present invention can utilize any suitable number and type of components to facilitate effective treatment of the patient by enhancing quality of life, economic, treatment efficiency and other like treatment conditions. For example, the present invention can employ the use of any number and acceptable type of pumps adapted in any suitable manner such that therapy solutions, including dialysate, can be effectively fed into, circulated within and drained from the single closed fluid loop connected to the patient.

Monitors

In an embodiment, the dialysis system of the present invention is a closed, sterile system in order to prevent air, moisture and other environmental contaminants from entering into the closed fluid loop. In this regard, the present invention can include a variety of different components to monitor for levels of contaminants in the system. For example, the present invention can include a gas sensor to monitor for atmospheric gases including oxygen and carbon dioxide. If detected, the present invention can include any suitable device to remove the gas from the system of the present invention such that the gas can be vented to the atmosphere.

In an embodiment, temperature sensors are provided at desired locations along the closed fluid loop. The temperature sensors monitor various fluid temperatures which can be utilized to control the fluid temperatures associated with the heater. When two or more heaters, such as an infrared heater and a plate heater, are provided in the dialysis system, the system in an embodiment includes separate temperature sensors for each heater so that each heater can be controlled individually.

The present invention in an embodiment also includes various other sensors to monitor various other parameters. For example, fluid pressure sensors can be electrically coupled to or otherwise communicate with a controller to provide a signal that indicates the respective fluid pressure at certain locations along the closed fluid path. Based on the signals from the pressure sensors, the controller can operate the fluid pumps and valves to obtain and maintain desired fluid pressures and flow rates in the loop running to, through and from the patient.

In an embodiment, the pressure sensors are non-invasive pressure sensors. These pressure sensors do not physically contact (and possibly contaminate) the medical fluid or dialysate. Of course other fluid flow measurement devices, such as flow rate sensors, pressure gauges, flowmeters, pressure regulators, orifice plates, mass flow meters, capacitative fluid sensor, or other flow measuring devices known to those of skill in the art may be provided in any suitable quantity and adapted to the fluid circuit.

In an embodiment, a flow measurement or volume sensing device is provided, which includes a capacitance sensor that measures the volume of fluid pumped through a chamber, such as a pump chamber (not shown). An example of the capacitive fluid sensor is disclosed in a patent assigned to the assignee of the present document and entitled, "Capacitance Fluid Volume Measurement," U.S. Pat. No. 7,107,837, incorporated herein by reference.

The capacitance C between two capacitor plates changes according to the function $C=k\times(S/d)$, wherein k is the dielectric constant, S is the surface area of the individual plates and d is the distance between the plates. The capacitance between the plates changes proportionally according to the function $1/(R\times V)$, wherein R is a known resistance and V is the voltage measured across the capacitor plates.

In an embodiment of the capacitance sensor, the sensor operates in cooperation with a cycler pump chamber. The cycler pump chamber in an embodiment includes shells or walls defining a fixed and known volume and a pair of flexible membranes operating between the shells, which expand to fill with fluid and contract to discharge fluid. The capacitance sensor includes capacitor plates disposed on opposite sides of the pump chamber. As the volume of fluid in the chamber or fluid pump changes (i.e., the pump chamber fills or empties), the dielectric property of the varying fluids between the capacitance plates changes. For example, the combined dielectric constant of dialysate and air changes as dialysate replaces air (or air replaces dialysate) within the constant volume shells of the chamber. This change in the overall dielectric constant affects a change in the capacitance between the two plates, which causes a change in voltage across the capacitance plates, wherein a corresponding change in voltage can be sensed by a voltage sensing device. The controller monitors the change in voltage by the voltage sensing device and correlates (after a calibration of the sensor) the capacitance change to an amount of fluid pumped through chamber.

In another embodiment, the volume of the chamber or the pump chamber can vary, e.g., by movement of one or both the shells of the chamber. In this embodiment, the capacitance between the capacitor plates changes due to a changing distance d between the plates and/or a changing surface area S of one or more of the plates, wherein the dielectric constant k is static because only one fluid resides at all times between the capacitor plates. In a further alternative embodiment of the measurement device, the capacitance C between the capacitor plates changes based on any combination of all three of a change in dielectric constant k, distance d and surface area S.

The controller collects a multitude of voltage signals from capacitance changes due to a plurality of chamber fill and drain cycles, wherein the controller calculates a total volume of medical fluid pumped over a length of time or number of pump cycles. The capacitance sensor monitors the medical fluid, e.g., dialysate, flow into or from the pump chamber on a real time basis, and in a non-invasive manner.

The capacitance sensor enables the dialysis system to maintain the volume of fluid that is provided to the patient at desirable amounts and flow rates. Maintaining the fluid flow to the patient within desired levels is particularly advantageous for peritoneal dialysis therapies.

It is also desirable to maintain the fluid provided to the patient at physiologic levels. Physiologic control, such as sensing and/or adjusting parameters of the fluids, can take place at various locations in the dialysis system. To this end, the system can include any combination of a number of different types of physiologic level sensors. For example, the system can include one or more pH sensors. In one implementation, the cartridges explained above in connection with FIG. 1 can include a pH sensor that helps to adjust the fluid so that it is maintained at a desired physiologic level.

Heater

The present invention can include a fluid heater which can adaptedly act to heat the fluid in the closed fluid loop to a desired temperature for supplying the fluid to the patient. In this regard, the temperature of the dialysate at initial system fill can be quite low, such as 5° C. to 10° C. if the fluid is stored in cold ambient temperature. In an embodiment, the fluid heater is an in-line heater (continuous flow heater) that heats the fluid to the desired temperature as the fluid flows continuously past the heater. In other embodiments, heaters other than in-line heaters can be used, for example, bulk heaters, a dual heater and the like.

In an embodiment, the fluid heater is a dual heater (not shown), including an infrared heater and a plate heater. An example of such a dual heater is disclosed in a patent application entitled, "Medical Fluid Heater Using Radiant Energy," Ser. No. 10/051,609, now U.S. Pat. No. 7,153,285, and incorporated herein by reference. Both the infrared heater and the plate heater are in-line heaters that heat the medical fluid that flows continuously past the heaters. The radiant energy or infrared heater emits infrared energy that is directed to and absorbed by the fluid in the patient loop, thereby heating the fluid. The radiant energy or infrared heater is a primary or high capacity heater which can heat a relatively large volume of cold fluid to a desired temperature in a short period of time.

The plate heater is a secondary or maintenance heater which has a relatively lower heating capacity relative to the infrared heater. The plate heater uses electrical resistance to increase the temperature of a plate that in turn heats the fluid flowing near the plate.

The heater, which includes both high and low capacity heaters, provides an efficient heater design that accommodates various fluid heating requirements. For example, the radiant or infrared heater is particularly useful for quickly heating cool dialysate (high heat energy demand) that is supplied to the dialysis system, such as at the initial system fill or if there is severe heat loss during dialysis treatment. The temperature of the dialysate at initial system fill can be quite low, such as 5° C. to 10° C. if the fluid is stored in cold ambient temperature.

The plate heater is particularly useful to maintain a desired temperature (lower heat energy demand) of the fluid being supplied to the patient, e.g., due to a normal amount of heat loss during dialysis treatment. The infrared heater provides for the high heat demand in a small amount of fluid exposure space, while the plate heater provides for maintenance heat demand and requires a lesser amount of input energy compared to the infrared or radiant heater. Furthermore, the heating capacity of the heater is increased if both the infrared and plate heaters are used together to heat the fluid.

The infrared heater and the plate heater can be arranged in various configurations relative to each other. The heaters in an embodiment are arranged so that the fluid passes by the heaters sequentially (e.g., first the radiant or infrared heater and then the plate heater or vice versa). In another embodiment, the fluid passes by the heaters simultaneously (both heaters at the same time). The fluid flow path past the heaters can be a common flow path for both heaters or include independent flow paths for each heater. Besides radiant or infrared electrical resistance heating, other types of heating such as convective, microwave, infrared ("IR") or inductive heating may be used.

Filter

The heater can include a number of different components. For example, the heater can include a filter made from any suitable material in any suitable filter size. The filter can be made of any suitable material and include any suitable filter size. In an embodiment, the filter is about 0.3 microns in size, preferably about 0.22 microns. This means that the filter can remove solutes in solutions that are about 0.3 microns in size or larger with a filter size of about 0.3 microns or about 0.22 microns in size or larger for a filter size of about 0.22 microns. The filter can act in a variety of different ways to enhance the performance of the dialysis system of the present invention.

For example, the filter can be used in place of typical UV decontamination techniques or the like to disinfect the therapy fluid prior to passing into, through and out of the patient. This can effectively eliminate, or at least greatly reduce, infection in the patient as a result of the treatment, such as peritonitis which can be contracted through touch contamination during therapy.

It should be appreciated that the filter(s) can be coupled to the fluid circuit at any suitable position. On the patient in flow side, the filter can act to disinfect the dialysate prior to passing into the patient as previously discussed. The filter(s) can also be coupled to the discharge pathway. In this location, the filter can be used to remove nutrients from the therapy fluid prior to discharge. The filter can then be cleaned by, for example, back flushing with a suitable solution, to remove the filtered nutrients for reuse and reintroduction into the patient. The filter can be constructed in any suitable way to enhance its filtering efficiency.

It should be appreciated that the fluid path, fluid circuit, fluid loop and/or the like of the present invention can be made of one or more fluid lines interconnected in any suitable manner. The fluid lines can include any suitable material including a flexible, sterile and inert plastic, such as polyethylene, polystyrene, polypropylene, polyvinyl chloride and/or combinations thereof. In general, the fluid lines are transparent such that the fluid flow through the lines can be visually observed.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention is claimed as follows:

1. A system for providing peritoneal dialysis to a patient, the system comprising:
   a catheter having an inflow lumen and an outflow lumen in communication with the patient's peritoneal cavity;
   a fluid circuit in fluid communication with the catheter thereby defining a closed fluid path capable of circulating a therapy fluid into, through and out of the peritoneal cavity;
   a first supply of the therapy fluid including a dialysate coupled to the fluid circuit;
   a cycler that pumps the dialysate into the fluid circuit and circulates the dialysate along the closed fluid path at a first flowrate during a treatment period to remove a therapeutically effective amount of solutes and ultrafiltrate from the patient;
   a second supply of the therapy fluid including an osmotic agent solution coupled to the fluid circuit wherein the cycler can pump the second supply of fluid into the fluid circuit during the treatment period;
   a cleaning device coupled to the fluid circuit wherein the cleaning device is capable of removing solutes including at least a portion of urea from the therapy fluid as it circulates along the closed fluid path, and
   a reservoir coupled fluidly to the fluid circuit via the cycler and one or more pumps and branching off the closed loop for moving fluid at a controlled second flowrate from the fluid circuit to the reservoir and from the reservoir to the fluid circuit, the second flowrate less than half of the first flowrate, and wherein the reservoir is adapted to provide a variable increase in volume capacity to the fluid circuit allowing the system to compensate for an increase in fluid volume in the fluid circuit during treatment.

2. The system of claim 1, wherein the treatment period comprises about eight hours or less.

3. The system of claim 1, wherein the first supply contains about 6 liters or less of dialysate.

4. The system of claim 1, wherein the second supply contains about 3 liters or less of the osmotic agent solution.

5. The system of claim 4, wherein the osmotic agent solution is selected from the group consisting of a 2.5% dextrose-based solution, a 3.5% dextrose-based solution, a 4.25% dextrose-based solution, a greater than 4.25% dextrose-based solution and combinations thereof.

6. The system of claim 1, wherein the osmotic agent solution contains about 4.25% or more of dextrose and one or more electrolytes at a concentration higher than existing levels in the fluid circulating through the fluid circuit.

7. The system of claim 6, wherein the second supply contains about 1 liter or less of the osmotic agent solution.

8. The system of claim 1, wherein the cleaning device is capable of non-selectively removing solutes from the therapy fluid.

9. The system of claim 8, wherein the cleaning device includes a sorbent material selected from the group consisting of carbon, activated charcoal, and combinations thereof in addition to a material capable of selectively removing at least a portion of the urea from the dialysate.

10. The system of claim 1, wherein the second flowrate is about one-third of the first flowrate.

11. A method of providing peritoneal dialysis to a patient, the method comprising the steps of:
    coupling a fluid circuit in fluid communication with a catheter in a peritoneal cavity of the patient thereby defining a closed fluid path along which a fluid is capable of being circulated to remove solutes and ultrafiltrate from the patient;
    supplying a source of the fluid including a dialysate from a container to the fluid circuit;
    circulating the dialysate along the closed fluid path;
    branching the container off the closed fluid path and communicating the container fluidly with a circulator of the dialysate via one or more pumps to increase a volume capacity of the fluid circuit to compensate for an increase in fluid volume in the fluid circuit by moving fluid from the fluid circuit to the container and from the container to the fluid circuit at controlled flowrates with the one or more pumps, and removing an amount of solutes from the fluid as the fluid circulates along the closed fluid path.

12. The method of claim 11, further comprising treating the patient for a period of about eight hours or less.

13. The method of claim 11, wherein about 6 liters or less of dialysate is supplied during treatment.

14. The method of claim 11, wherein about 1.5 liters or less of ultrafiltrate is added to the fluid circuit during treatment.

15. The method of claim 11, wherein a sorbent material including carbon is employed to non-selectively remove the solutes from the dialysate.

16. The method of claim 11, wherein at least a portion of urea is selectively removed from the dialysate.

17. The method of claim 11, wherein the peritoneal dialysis treatment is provided to the patient at the patient's home.

18. A method of providing peritoneal dialysis to a patient, the method comprising the steps of:
coupling a fluid circuit in fluid communication to a catheter in a peritoneal cavity of the patient thereby defining a closed fluid path along which a therapy fluid is capable of being circulated to remove solutes and ultrafiltrate from the patient;
supplying a first source of a therapy fluid including a dialysate from a container to the fluid circuit;
supplying a second source of the therapy fluid including an osmotic agent solution to the fluid circuit;
circulating the therapy fluid along the closed fluid path;
branching the container off the closed fluid path and communicating the container fluidly with a circulator of the therapy fluid from the fluid circuit to the container and from the container to the fluid circuit at a controlled flowrate to increase a volume capacity of the fluid circuit to compensate for an increase in fluid volume due to the ultrafiltrate and the osmotic agent solution, and
removing an amount of solutes including a therapeutically effective portion of urea from the therapy fluid as the therapy fluid circulates.

19. The method of claim 18 further comprising treating the patient for a period of about eight hours or less.

20. The method of claim 18 wherein about 6 liters or less of the dialysate is added to the fluid circuit during treatment.

21. The method of claim 18 wherein about 1.5 liters or less of ultrafiltrate is added to the fluid circuit during treatment.

22. The method of claim 18 wherein about 3 liters or less of the osmotic agent solution is added to the fluid circuit during treatment in which the osmotic agent solution is selected from the group consisting of a 2.5% dextrose-based solution, a 3.5% dextrose-based solution, a 4.25% dextrose-based solution, a greater than 4.25% dextrose-based solution and combinations thereof.

23. The method of claim 18 wherein about 1 liter or less of the osmotic agent solution is added to the fluid circuit during treatment in which the osmotic agent solution contains about 4.25% or more of dextrose.

24. The method of claim 18 wherein a sorbent material including carbon is employed to non-selectively remove solutes from the therapy fluid in addition to a material capable of selectively removing at least a portion of urea from the therapy fluid.

25. The method of claim 18, wherein the peritoneal dialysis treatment is provided to the patient at the patient's home.

26. A method for providing peritoneal dialysis to a patient, the method comprising the steps of:
coupling a fluid circuit in fluid communication to a catheter in a peritoneal cavity of the patient thereby defining a closed fluid path along which a therapy fluid is capable of being circulated to remove solutes and ultrafiltrate from the patient;
supplying a therapy fluid including a dialysate from a reservoir to the fluid circuit;
circulating the therapy fluid along the closed fluid path,
replenishing the therapy fluid within the closed fluid bath by removing an amount of solutes from the therapy fluid as the therapy fluid circulates and supplying an osmotic agent solution to the fluid circuit in amount sufficient to replenish diffusive properties of the therapy fluid during treatment; and
moving the therapy fluid at a controlled flow rate from the fluid circuit to the reservoir and from the reservoir to the fluid circuit to compensate for an increase in fluid volume in the fluid circuit during treatment.

27. The method of claim 26 wherein about 3 liters or less of the osmotic agent solution is added to the fluid circuit during treatment in which the osmotic agent solution is selected from the group consisting of a 2.5% dextrose-based solution, a 3.5% dextrose-based solution, a 4.25% dextrose-based solution, a greater than 4.25% dextrose-based solution and combinations thereof.

28. The method of claim 27 wherein about 2 liters or less of the osmotic agent solution is added to the fluid circuit during treatment.

29. The method of claim 26 wherein about 1 liter or less of the osmotic agent solution is added to the fluid circuit during treatment in which the osmotic agent solution contains about 4.25% or more of dextrose.

30. The method of claim 26 wherein a sorbent material including carbon is employed to non-selectively remove solutes from the therapy fluid.

31. The method of claim 26 wherein the removal of the amount of solutes includes a removal of at least a portion of urea from the therapy fluid.

32. The method of claim 26, the method further comprising:
sensing the level of ultrafiltrate removed from the patient, and
adjusting the level of osmotic agent solution supplied to the fluid circuit to either increase or decrease the level of ultrafiltrate removed from the patient.

* * * * *